United States Patent [19]

Fanney et al.

[11] Patent Number: 5,800,396

[45] Date of Patent: *Sep. 1, 1998

[54] SURGICAL CASSETTE ADAPTER

[75] Inventors: Douglas M. Fanney, Oceanside; Valentine P. Injev, Irvine; Richard A. Rossback, Irvine; Gary P. Sorensen, Irvine, all of Calif.

[73] Assignee: Alcon Laboratories, Inc., Fort Worth, Tex.

[*] Notice: This patent issued on a continued prosecution application filed under 37 CFR 1.53(d), and is subject to the twenty year patent term provisions of 35 U.S.C. 154(a)(2).

[21] Appl. No.: 558,308

[22] Filed: Nov. 15, 1995

[51] Int. Cl.⁶ ............................................. A61M 5/00
[52] U.S. Cl. ............................................. 604/151; 604/30
[58] Field of Search ............................ 604/27, 30, 131, 604/151, 152, 153

[56] References Cited

U.S. PATENT DOCUMENTS

| | | |
|---|---|---|
| 4,367,736 | 1/1983 | Gupton ........................... 604/30 |
| 4,395,258 | 7/1983 | Wang et al. . |
| 4,444,198 | 4/1984 | Petre ........................... 604/30 X |
| 4,493,695 | 1/1985 | Cook . |
| 4,627,833 | 12/1986 | Cook . |
| 4,713,051 | 12/1987 | Steppe et al. . |
| 4,756,706 | 7/1988 | Kerns et al. . |
| 4,758,238 | 7/1988 | Sundblom et al. . |
| 4,790,816 | 12/1988 | Sundblom et al. . |
| 4,798,580 | 1/1989 | DeMeo et al. . |
| 5,009,641 | 4/1991 | Gorton ........................... 604/131 |
| 5,106,366 | 4/1992 | Steppe ........................... 604/30 |
| 5,163,900 | 11/1992 | Wortrich ........................... 604/30 |
| 5,230,614 | 7/1993 | Zanger et al. . |
| 5,249,121 | 9/1993 | Baum et al. . |
| 5,267,956 | 12/1993 | Beuchat . |
| 5,268,624 | 12/1993 | Zanger . |
| 5,328,456 | 7/1994 | Horiguchi et al. . |
| 5,364,342 | 11/1994 | Beuchat et al. . |
| 5,387,088 | 2/1995 | Knapp et al. . |
| 5,392,653 | 2/1995 | Zanger et al. . |
| 5,403,277 | 4/1995 | Dodge et al. ........................... 604/30 |
| 5,417,246 | 5/1995 | Perkins et al. . |
| 5,460,490 | 10/1995 | Carr et al. . |
| 5,494,036 | 2/1996 | Uber, III et al. ........................... 604/131 X |

FOREIGN PATENT DOCUMENTS 0 529 902 A2   3/1993   European Pat. Off. .

*Primary Examiner*—John D. Yasko
*Attorney, Agent, or Firm*—Jeffrey S. Schira

[57] ABSTRACT

A self-contained adapter that is connected to a surgical console. The adapter contains all of the components necessary to allow different cassettes to be used with the surgical console.

8 Claims, 7 Drawing Sheets

SURGICAL CASSETTE ADAPTER

BACKGROUND OF THE INVENTION

The present invention relates to surgical cassettes and more particularly to a surgical cassette adapter.

The use of cassettes with surgical instruments to help manage irrigation and aspiration flows into a surgical site are well-known. U.S. Pat. Nos. 4,493,695, 4,627,833 (Cook), 4,395,258 (Wang, et al.), 4,713,051 (Steppe, et al.), 4,798,850 (DeMeo, et al.), 4,758,238, 4,790,816 (Sundblom, et al.) and 5,267,956, 5,364,342 (Beuchat) all disclose tubeless or tube-type surgical cassettes and are incorporated herein in their entirety by reference.

The fluidic performance of the surgical instrument is substantially affected by the fluidic performance of the cassette. As a result, prior art surgical instruments and cassettes are designed to work as an integral system, with the fluidic performance of the cassette designed to optimize the fluidic performance of the entire surgical system. This integral design concept has required that prior art surgical instruments be used with only one specific cassette. While the dedication of a surgical instrument to a particular cassette normally does not pose any particular problems with the surgeon or in any way affect the surgical outcome, each cassette normally has certain advantages and contains certain compromises (i.e., fluidic performance, cost, reusability, etc.). Therefore, under certain circumstances, it is desirable to use a cassette designed to be used with a specific surgical console on a different console. Prior to the present invention, adapters permitting such interchangeability were not available.

Accordingly, a need continues to exist for a device that enables a surgical console designed for use with a first cassette to be used with a second cassette.

BRIEF DESCRIPTION OF THE INVENTION

The present invention is a self-contained adapter that may be connected to a surgical console. The adapter contains all of the components necessary to allow different cassettes to be used with the surgical console.

Accordingly, one objective of the present invention is to provide a cassette adapter.

Another objective of the present invention is to provide a device that enables a cassette designed for use with a first surgical console to be used with a second surgical console.

These and other objectives and advantages of the present invention will become apparent from the detailed description and claims which follow.

DETAILED DESCRIPTION OF THE INVENTION

Figure 7:
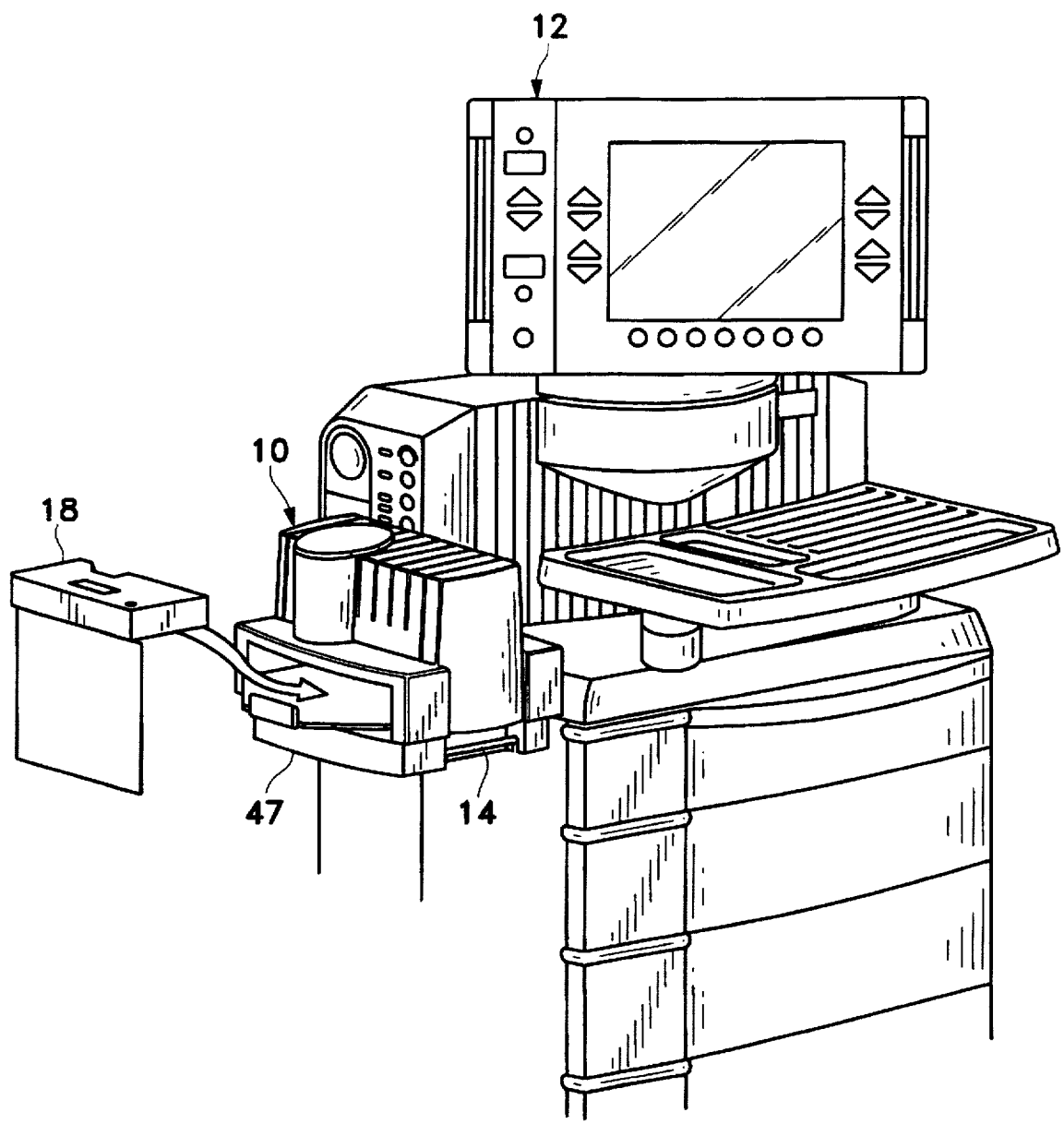
FIG. 7 is a perspective view of the present invention similar to FIG. 1 and illustrating the present invention attached to a surgical console.
Figure 8:
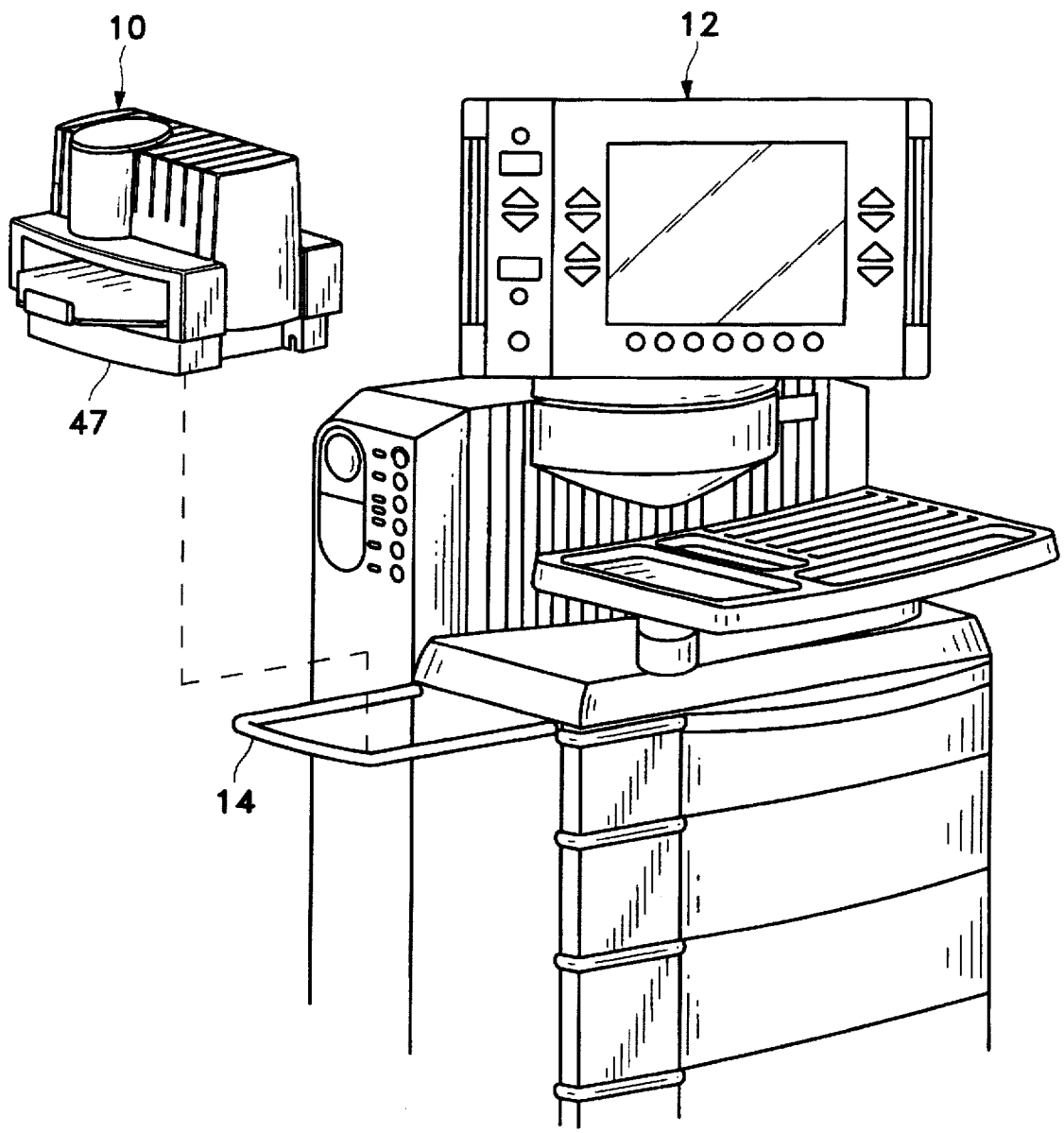
FIG. 8 is an expanded perspective view of the present invention similar to FIG. 7 and illustrating the present invention attaching to a surgical console.

As best seen in FIGS. 7 and 8, adapter 10 of the present invention preferably is a separate enclosed unit designed to be supported mechanically adjacent to surgical console 12. While any suitable surgical console 12 may be used the SERIES TWENTY THOUSAND® LEGACY® PHACO-EMULSIFIER® surgical console, manufactured by Alcon Laboratories, Inc., Fort Worth, Tex., is preferred. Other suitable consoles are described in U.S. Pat. Nos. 5,249,121 (Baum, et al.), 5,268,624 (Zanger), 5,392,653 (Zanger, et al.) and 5,417,246 (Perkins, et al.), the entire contents of which are incorporated herein by reference. Adapter 10 may be supported on console 12 by any suitable method, such as slide out bail 14 on console 12 interacting with bottom enclosure 47, which is secured to mounting bracket 24 on adapter 10.

As best seen in FIGS. 1, 2, 3, 5 and 7, adapter 10 contains platform 16 that receives external cassette 18. One suitable cassette 18 is described in U.S. Pat. No. 4,713,051 (Steppe, et al.) (hereinafter the "Steppe" cassette), but other suitable cassettes 18, such as those described in the patents listed above, may also be used in combination with the present invention by the appropriate modifications to adapter 10.

Figure 5:
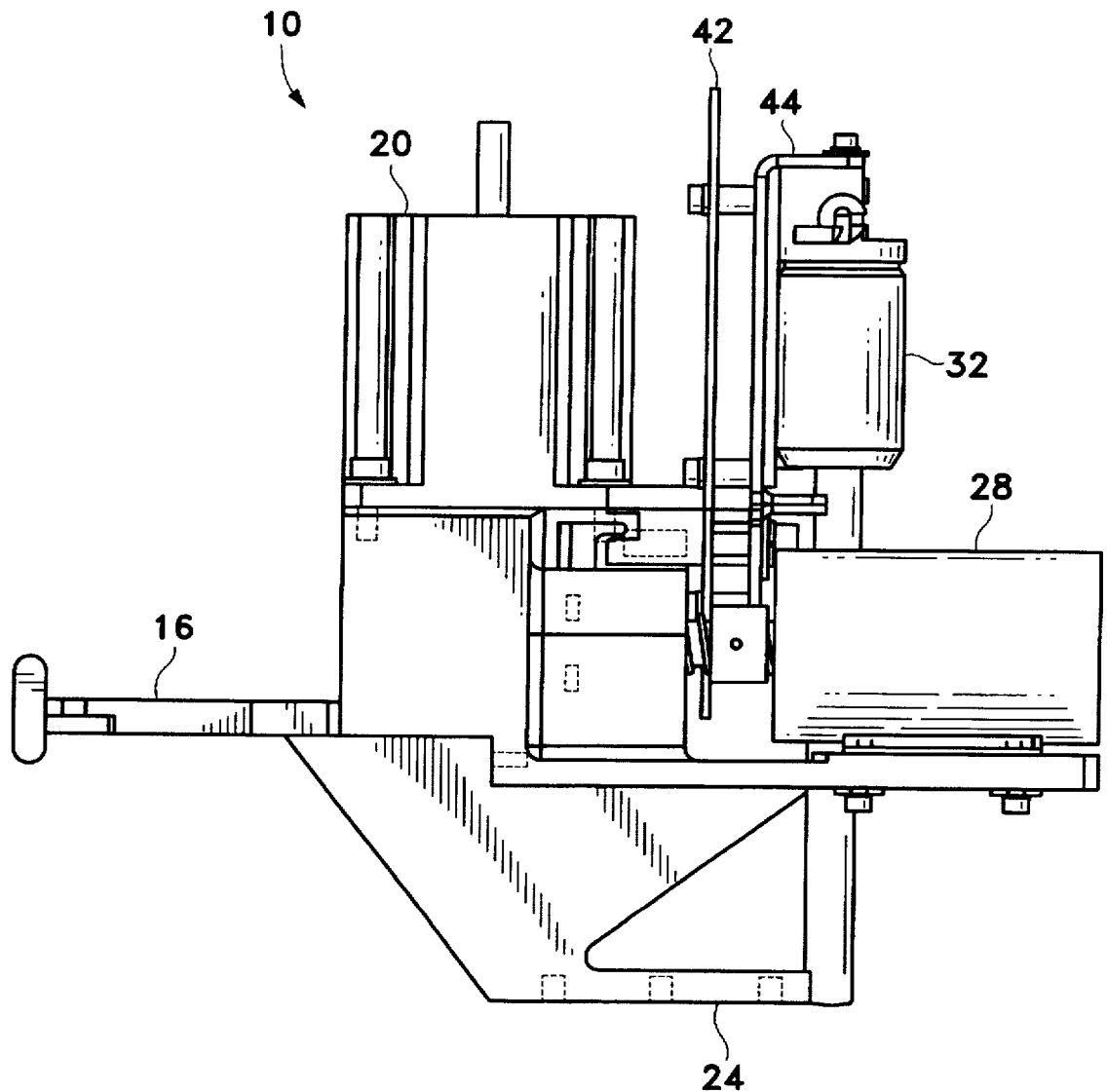
FIG. 5 is a left elevational view of the embodiment of the present invention illustrated in FIG. 1 with the outer housing removed.
Figure 6:
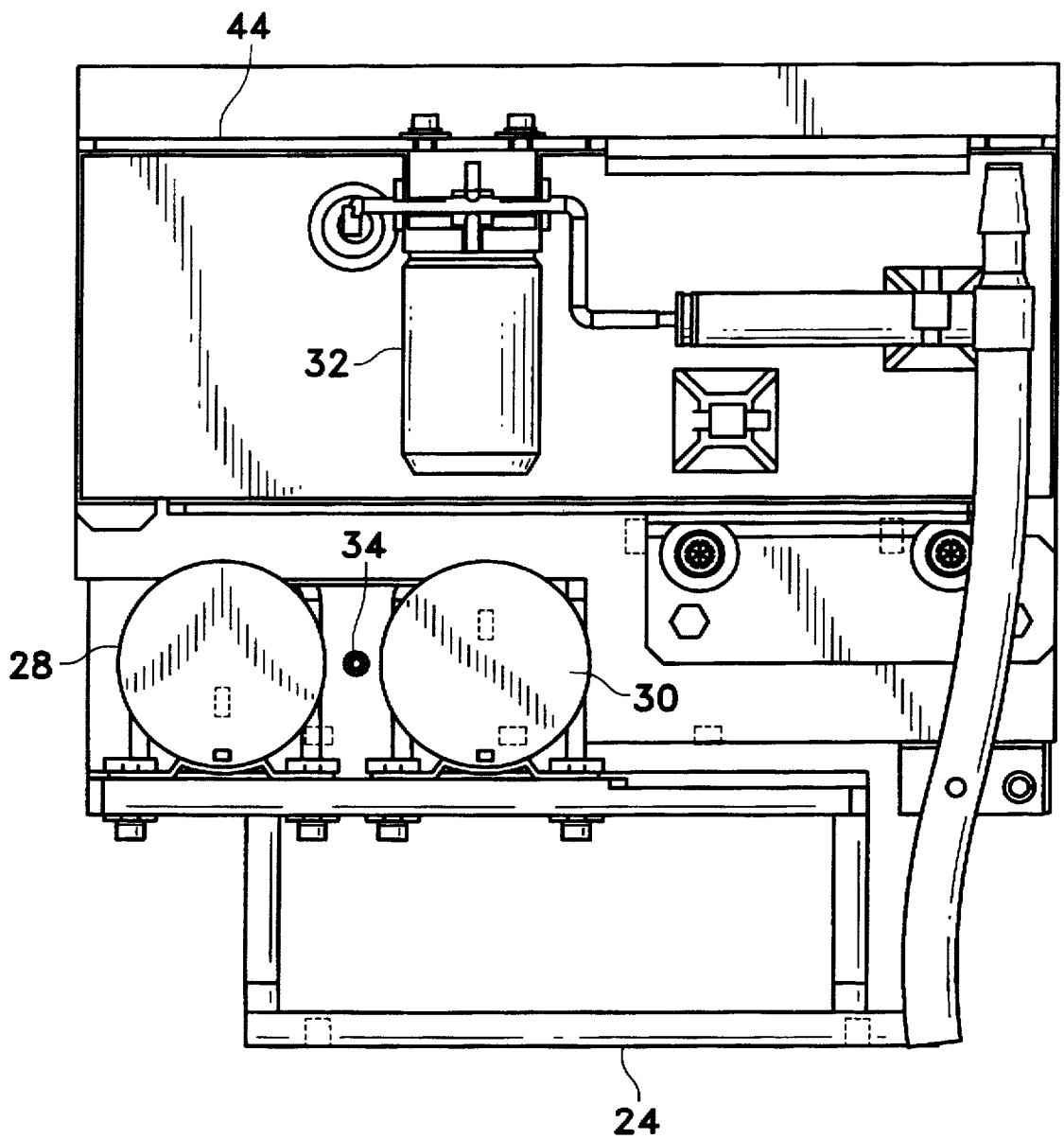
FIG. 6 is a rear elevational view of the embodiment of the present invention illustrated in FIG. 1 with the outer housing removed.

Adapter 10 includes all of the mechanical and electrical components necessary to allow cassette 18 to be used in combination with console 12. For example, as seen in FIGS. 5 and 6, if cassette 18 is of a peristaltic pump design (such as the Steppe cassette), then adapter 10 may contain motor 20 that rotates peristaltic pump roller head 22. If cassette 18 is of a diaphragm or venturi design, then adapter 10 may contain a diaphragm pump (not shown) or a venturi pump (not shown). Other components of adapter 10 may include irrigation solenoid 28, vent solenoid 30 and purge valve 32. Purge valve 32 communicates with cassette 18 through port 34 and allows monitoring of the aspiration pressure within cassette 18. Irrigation solenoid 28 pinches the irrigation lines (not shown) within cassette 18 to control the flow of irrigation fluid to the surgical site. Vent solenoid 30 pinches the vent line (not shown) within cassette 18 to control the aspiration pressure within cassette 18. A more complete discussion of the operation of Steppe-type cassettes 18 is contained in U.S. Pat. No. 4,713,051.

While the above discussion relates to the use of a Steppe-type cassette 18, it will be appreciated that other suitable mechanical and electrical controls may be used in adapter 10. For example, adapter 10 may include the devices described in U.S Pat. Nos. 5,387,088 (Knapp, et al.), 5,328,456 (Horiguchi, et al.) and 5,230,614 (Zanger, et al.), the entire contents of which are incorporated herein by reference.

Adapter 10 operates under the control of signals generated by PCB 42, which is mounted on bracket 44 within adapter 10. PCB 42 preferably contains an INTEL® 80196, but other suitable microprocessors may also be used. One suitable block diagram for PCB 42 is illustrated in FIG. 4.

Figure 1:
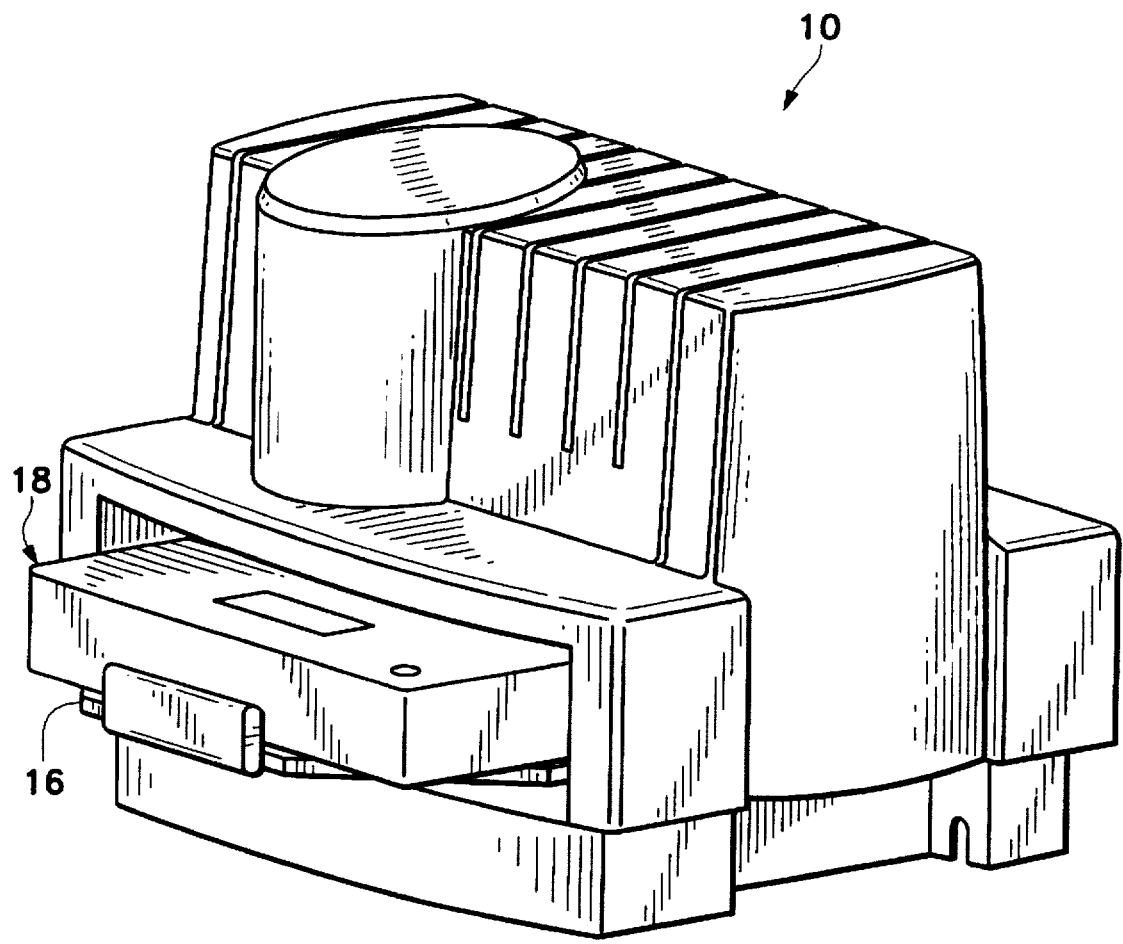
FIG. 1 is a perspective view of one embodiment of the present invention.
Figure 2:
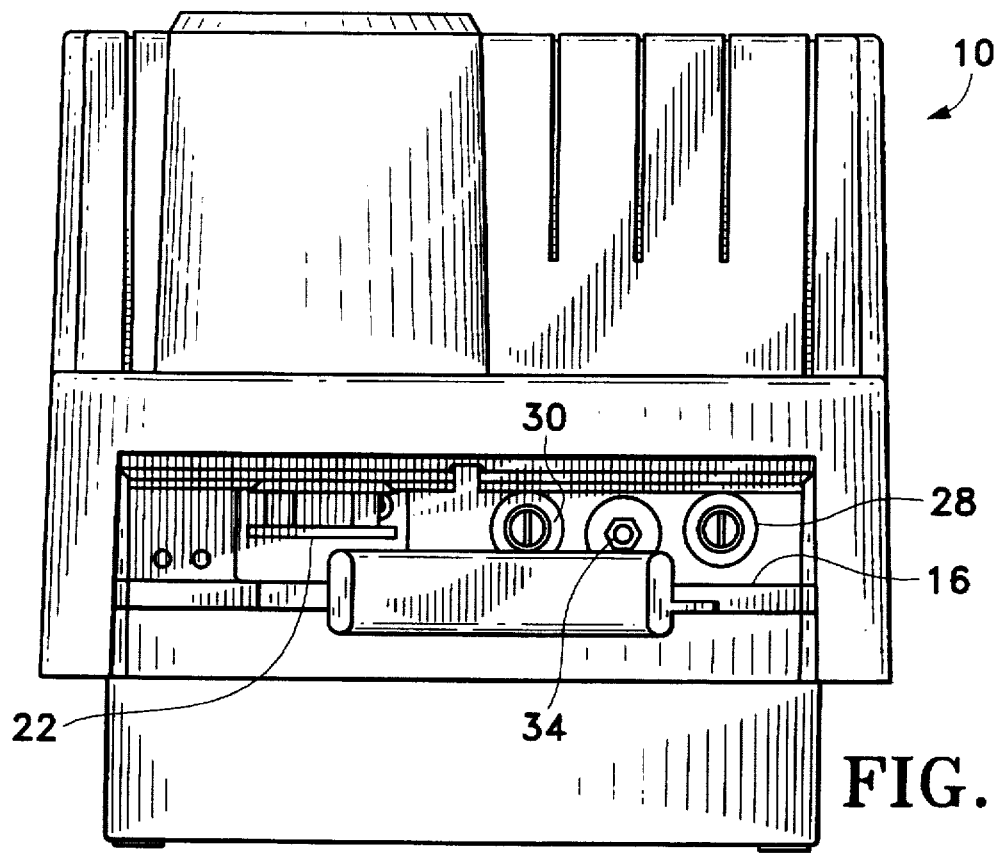
FIG. 2 is a front elevational view of the invention illustrated in FIG. 1.
Figure 3:
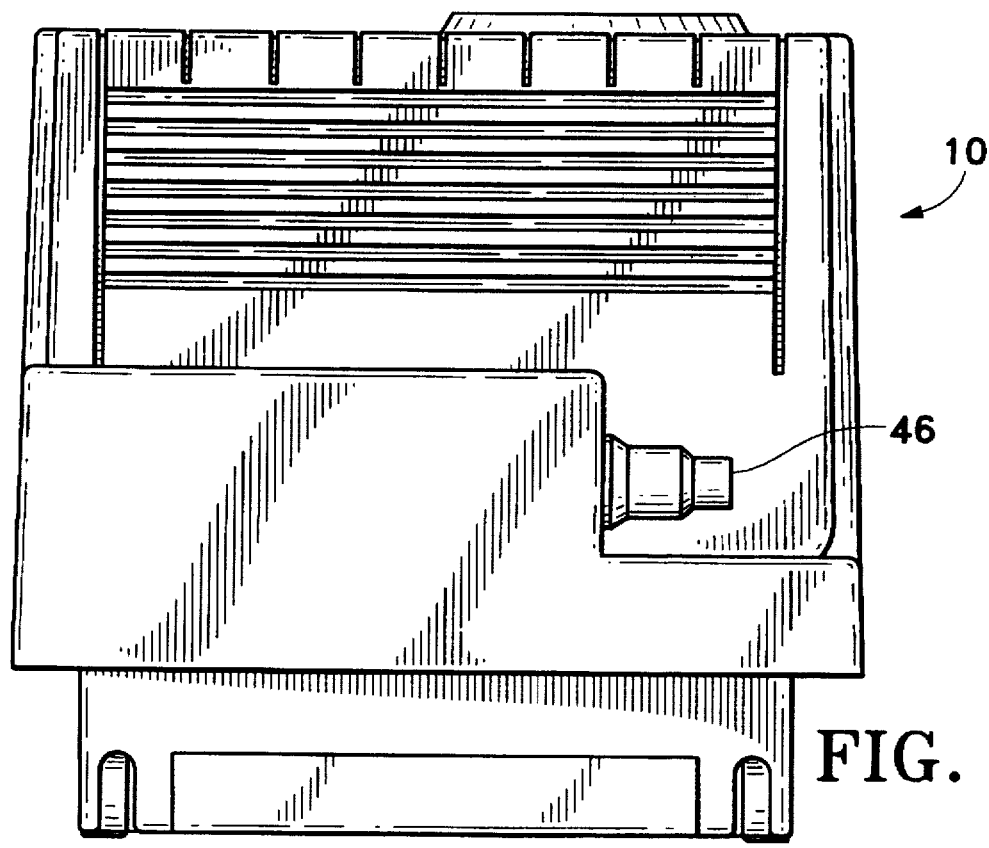
FIG. 3 is a rear elevational view of the invention illustrated in FIG. 1.
Figure 4:
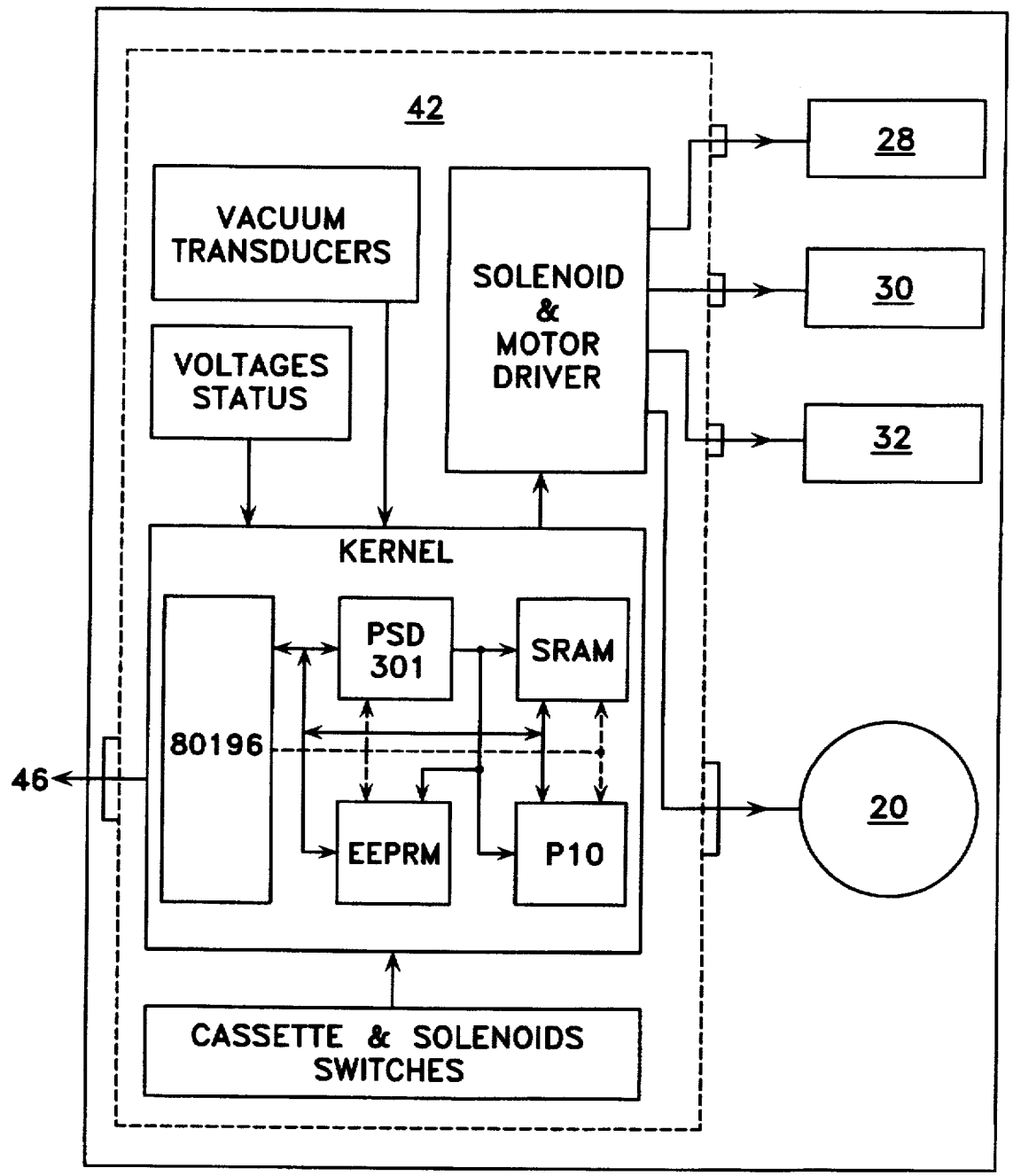
FIG. 4 is an electrical block diagram of one embodiment of the present invention.

As seen in FIGS. 3 and 4, communications, power and control signals are provided between adapter 10 and console 12 through a cable (not shown) connected to port 46 on adapter 10. As a result, it is not necessary to duplicate in adapter 10 all of the control circuitry, user interface controls and power supplies that are contained in console 12.

This description is given for purposes of illustration and explanation. It will be apparent to those skilled in the relevant art that changes and modifications may be made to the invention described above without departing from its scope or spirit.

We claim:

1. A surgical cassette adapter, comprising:

a) a housing adapted to receive a surgical cassette, the housing designed to be supported mechanically on a surgical console;

b) a means contained within the housing for controlling irrigation fluid flow within the cassette;

c) a means contained within the housing for controlling aspiration fluid flow within the cassette; and d) a communications port connected to both the means for controlling irrigation fluid flow within the cassette and the means for controlling aspiration fluid flow within the cassette.

2. The surgical cassette adapter of claim 1 wherein the means contained within the housing for controlling aspiration fluid flow within the cassette comprises a motor driving a peristaltic pump roller head, and at least one solenoid.

3. The surgical cassette adapter of claim 1 wherein the adapter is electrically connected to the surgical console.

4. The surgical cassette adapter of claim 1 wherein the surgical cassette is a Steppe-type surgical cassette.

5. A surgical system, comprising:

a) a surgical console;

b) a surgical cassette; and c) an adapter that receives the surgical cassette, the adapter designed to be supported mechanically on the surgical console.

6. The surgical system of claim 5 wherein the adapter comprises a motor driving a peristaltic pump roller head, and at least one solenoid.

7. The surgical system of claim 5 wherein the adapter is electrically connected to the surgical console.

8. The surgical system of claim 5 wherein the surgical cassette is a Steppe-type surgical cassette.

* * * * *